United States Patent [19]

Okada

[11] Patent Number: 4,741,335

[45] Date of Patent: May 3, 1988

[54] CALCULUS CRUSHING APPARATUS

[75] Inventor: Tsutomu Okada, Tokyo, Japan

[73] Assignee: Olympus Optical Co., Ltd., Tokyo, Japan

[21] Appl. No.: 4,769

[22] Filed: Jan. 9, 1987

Related U.S. Application Data

[63] Continuation of Ser. No. 696,596, Jan. 31, 1985, abandoned.

[30] Foreign Application Priority Data

Feb. 3, 1984 [JP] Japan ................................. 59-17802
May 17, 1984 [JP] Japan ................................. 59-99607

[51] Int. Cl.<sup>4</sup> ............................................. A61B 17/22
[52] U.S. Cl. .................................... 128/320; 128/328
[58] Field of Search ............... 128/328, 320, 321, 356, 128/304, 345

[56] References Cited

U.S. PATENT DOCUMENTS 1,002,826  9/1911  Vilbiss ................. 128/312
4,256,113  3/1981  Chamness .
4,294,254  10/1981  Chamness .

FOREIGN PATENT DOCUMENTS

3206846  4/1984  Fed. Rep. of Germany .

Primary Examiner—Michael H. Thaler

[57] ABSTRACT

A crushing apparatus has a flexible sheath which is adapted to be inserted into a body cavity with the aid of an endoscope. An operating wire longer than the sheath is slidably inserted into the sheath. A collapsible basket for seizing a calculus produced in a body cavity is coupled to the distal end of the operation wire and extends from the sheath. The proximal end of the sheath is connected to an operating section for sliding the operating wire to extend or contract the basket. The operating section includes a rack coupled to the operating wire and an operating handle connected to the rack through a speed reduction mechanism. The reduction mechanism decelerates and transmits an operative force, which is supplied to the handle, to the rack, thereby sliding the operating wire.

7 Claims, 7 Drawing Sheets

CALCULUS CRUSHING APPARATUS

This application is a continuation of application Ser. No. 696,596, filed Jan. 31, 1985, now abandoned.

BACKGROUND OF THE INVENTION

The present invention relates to a calculus crushing apparatus for crushing a calculus produced in a body cavity.

Calculi produced in internal organs, such as the bile duct, bladder, etc., greatly endanger the health of, and cause great pain to, patients.

To rid patients of their calculi, a method is conventionally used in which a calculus crushing apparatus is inserted into the body with the aid of an endoscope, whereby calculi produced in the body are crushed and eliminated from the body or extracted whole.

In one such prior art crushing apparatus, a basket formed of a plurality of elastic wires and adapted to seize foreign substances is fixed to the distal end of an operating wire, and the operating wire, along with the basket thereon, is inserted into a flexible sheath which has a rigid portion at its distal end, and is caused to advance or retreat from behind the rear end of the sheath, thereby extending or contracting the basket. After a calculus is seized by the basket projected from the distal end of the flexible sheath, the basket is drawn into the sheath to be collapsed by operating the operating wire. Thus, the calculus in the basket is crushed into small pieces.

In the calculus crushing apparatus of this type, as disclosed in, e.g., Japanese Utility Model Disclosure No. 55-34810, the operating wire for operating the basket is controlled by a slide mechanism. When drawing in the operating wire by the use of such a slide mechanism, there is no problem in regards to the operation before the crushing of the calculus. After the calculus is crushed by the contracted basket, however, the operating wire is released from resistance thereon for an instant, so that the basket will be quickly drawn into the flexible sheath. When this happens, fine pieces of the crushed calculus forcibly scatter, causing prossible injury to the inner wall of the body cavity.

SUMMARY OF THE INVENTION

The present invention is contrived in consideration of these circumstances, and is intended to provide a calculus crushing apparatus capable of safely crushing calculi.

In order to achieve the above objects, according to a crushing apparatus of the present invention, operating means for sliding an operating wire to open or close a basket includes slidable interlocking means coupled to the proximal end portion of the operating wire and drive means including a speed reduction mechanism engaging the interlocking means and adapted to decelerate and transmit an operative force to the interlocking means, thereby advancing and retreating the operating wire.

Thus, according to the crushing apparatus of the invention, the operative force is transmitted to the operating wire after it is decelerated, so that a calculus in the basket can be crushed gradually. Therefore, the operating wire and basket can be prevented from moving quickly at the moment the crushing of the calculus is caused, so that scattering of the calculus can be avoided.

BRIEF DESCRIPTION OF THE DRAWINGS

FIGS. 1 to 7 show a crushing apparatus according to one embodiment of the present invention, in which

FIGS. 8 to 10 show a crushing apparatus according to a second embodiment of the invention, in which

DETAILED DESCRIPTION OF THE PREFERRED EMBODIMENTS

Preferred embodiments of the present invention will now be described in detail with reference to the accompanying drawings.

Figure 1:
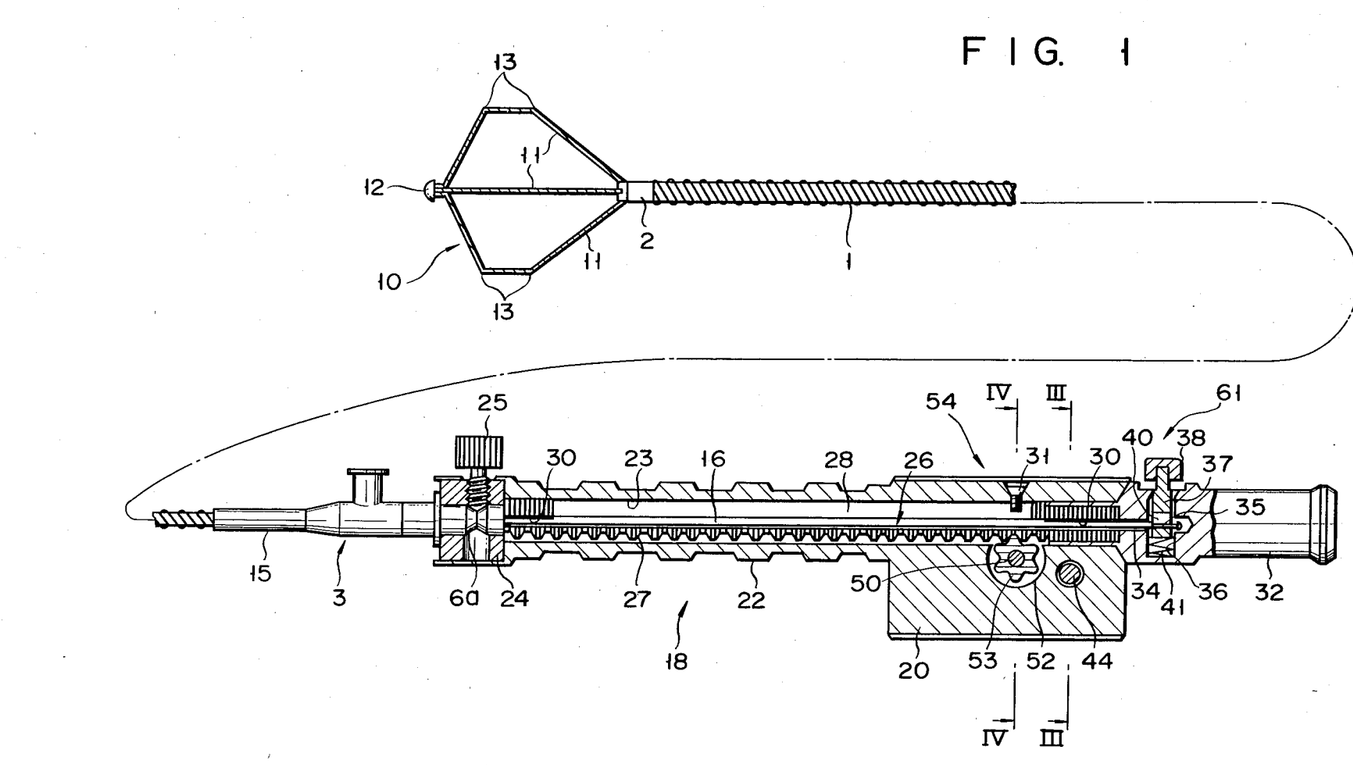
FIG. 1 is a cutaway side view showing an outline of the apparatus.
Figure 2:
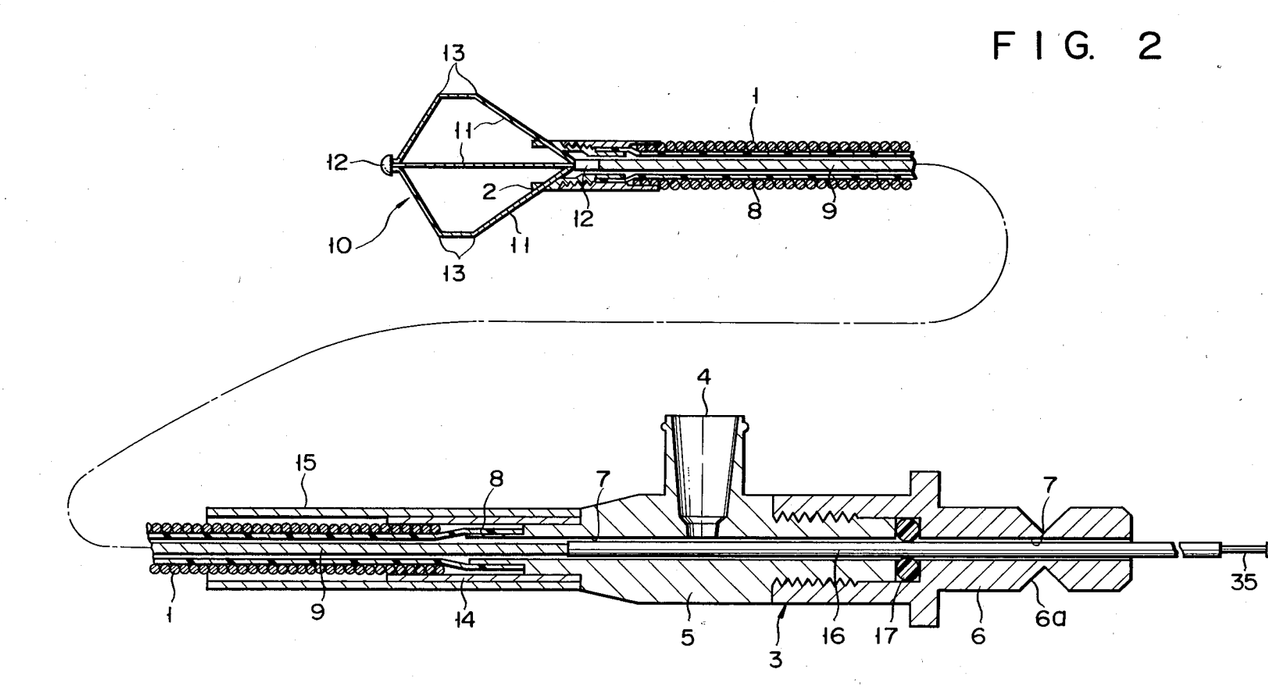
FIG. 2 is a sectional view of a flexible sheath used in the apparatus.

As shown in FIGS. 1 and 2, a calculus crushing apparatus according to one embodiment of the present invention is provided with a flexible sheath 1 which is formed of, e.g., a closely wound coil. A tubular rigid portion 2 formed of stainless steel or the like is attached to the distal end of the sheath 1, and a connector 3 to the proximal end. As shown in FIG. 2, the connector 3 includes a first member 5 having a liquid inlet port 4 and a second member 6 screwed onto the first member 5. Holes 7 coaxially penetrate both members 5 and 6 forming a straight passage through the complete length of connector 3 when members 5 and 6 are screwed together. A liquid-tight tube 8 inserted in the sheath 1 is connected to the first member 5, communicating with the through hole 7. Thus, a syringe (not shown) can be connected to the liquid inlet port 4 of the connector 3 so that a liquid such as a contrast medium can be fed into the tube 8. The proximal end portion of the sheath 1 is fixed in a mounting sleeve 14 which extends from the first member 5. Further, the proximal end portion of the sheath 1 is protected by a cover 15 which is disposed outside the mounting sleeve 14.

An operating wire 9 which is longer than the flexible sheath 1 is movably inserted in the sheath. The distal end of the operating wire 9, i.e., the end on the side of the rigid portion 2 of the flexible sheath 1, is fitted with a basket 10 for seizing and crushing a calculus. More specifically, the basket 10 is constructed by connecting each end of a plurality of elastic wires 11 by means of chips 12 and forming a bent portion 13 at the middle portion of each wire 11. Thus, the basket 10 is collapsible or closable in the axial direction of the operating wire 9.

The forward end of an elongate, straight coupling rod 16 is fixed to the proximal end of the operating wire 9 which projects from the rear end of the flexible sheath 1. The coupling rod 16 is slidably inserted into the through hole 7 of the connector 3. The rear end portion of the coupling rod 16 projects from the second member 6. An O-ring 17 is disposed at the junction between the first and second members 5 and 6 of the connector 3, whereby the through hole 7 is kept liquid-tight. The coupling rod 16 penetrates the O-ring 17.

The connector 3 is detachably connected to an operating section 18. As seen from FIG. 1, the operating section 18 includes a body 20 and a grip portion 22 extending from the body and adapted to be grasped by an operator. The body 20 and the grip portion 22 are penetrated by an insertion hole 23 which extends along the extending direction of the grip portion 22. A connecting ring 24 is attached to the forward end of the grip portion 22 so as to be coaxial with the insertion hole 23. A setscrew 25 is screwed in the ring 24 so as to be able to advance and retreat in the radial direction of the ring 24. The connector 3 can be coupled to the operating section 18 by inserting the rear end portion of the second member 6 of the connector into the connecting ring 24 and screwing the setscrew 25 into the connecting ring 24 so that the tip end of the setscrew is fitted in a groove 6a formed in the peripheral surface of the rear end portion of the second member. The coupling rod 16 is inserted into the insertion hole 23 by connecting the connector 3 to the operating section 18.

Figure 3:
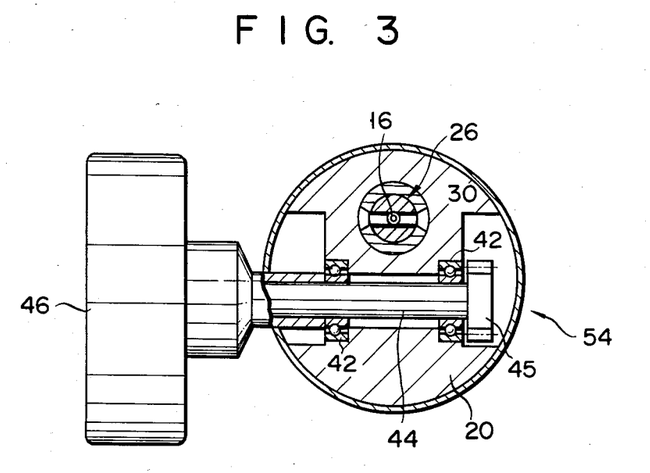
FIG. 3 is a sectional view taken along line III—III of FIG. 1.
Figure 4:
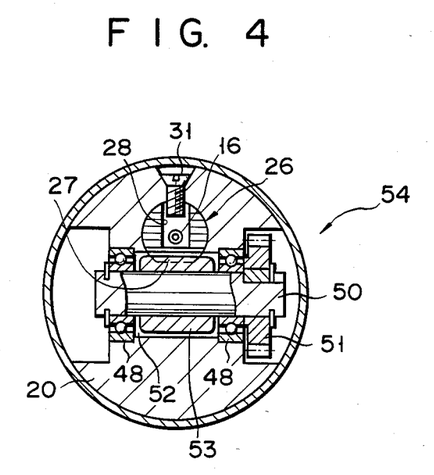
FIG. 4 is a sectional view taken along line IV—IV of FIG. 1, and FIGS. 5, 6 and 7 are schematic side views for illustrating the operation of the apparatus.

As shown in FIGS. 1, 3 and 4, a rack 26 is slidably inserted into the insertion hole 23 of the operating section 18. The rack 26 has a substantially circular cross section, and teeth 27 are formed on one side of the rack 26 with respect to its diametrical direction over the substantially whole axial length. A guide groove 28 is formed in the whole region of the rack 26 except both end portions thereof, opening to the outer surface of the rack on the opposite side to the teeth 27 and extending along the axial direction of the rack. Through holes 30 are formed individually in the two end portions of the rack 26 so as to be coaxial with the insertion hole 23 and to communicate with the guide groove 28. A guide screw 31 screwed into the body 20 of the operating section 18 engages the guide groove 28 of the rack 27, thereby preventing the rack 27 from rocking in the insertion hole 23. The rear end portion of the coupling rod 16 extending from the connector 3, is inserted into the through holes 30 and the guide groove 28 so that its extreme end projects from the rear end of the rack 26.

A handle grip portion 32 for sliding the rack 26 is coupled to the rear end of the rack, extending from the body 20 of the operating section 18. The handle grip portion 32 is formed with a mounting hole 34, coaxial with the through holes 30 of the rack 26 and communicating with the guide groove 28 by means of one of the through holes 30. The extreme end of the coupling rod 16 formed with a flat portion 35 (see FIGS. 1 and 2) is inserted in the mounting hole 34. A housing hole 36 is formed in the handle grip portion 32 along the diametrical direction thereof. The housing hole 36 crosses the mounting hole 34 and opens to the outer surface of the handle grip portion 32. The housing hole 36 receives a retaining rod 37 which is fitted with a button 38 at its top end. The retaining rod 37 has an engaging hole 40 bored through its middle portion, and is urged to project from the handle grip portion 32 by a spring 41 in the housing hole 36. First, the retaining rod 37 is pressed in against the urging force of the spring 41 to align the engaging hole 40 with the mounting hole 34. In this state, the extreme end of the coupling rod 16 is inserted into the mounting hole 34 to locate the flat portion 35 in the engaging hole 40. Then, if the pressure on the retaining rod 37 is removed therefrom, the flat portion 35 of the coupling rod 16 engages the retaining rod 37, so that the coupling rod 16 is coupled to the handle grip portion 32. Thus, the operating wire 9 can be advanced or retreated by means of the coupling rod 16, by operating the handle portion 32.

As shown in FIGS. 1 and 3, a first support shaft 44 is rotatably supported on the body 20 of the operating section 18 by bearings 42, extending at right angles to the rack 26. A first gear 45 is fixed to one end of the support shaft 44, while a handle 46 disposed outside the body 20 is attached to the other end. As shown in FIG. 4, moreover, a second support shaft 50 is rotatably supported on the body 20 by bearings 48, extending parallel to the first support shaft 44. The second support shaft 50 is fitted at one end with a second gear 51 which has more teeth than the first gear 45 and is in mesh with the first gear. The body 20 is formed with a cavity 52 which is located on the side of the teeth 27 of the rack 26 and opens into the insertion hole 23. The second support shaft 50 extends through the cavity 52. A third gear 53 fitted on the second support shaft 50 is housed in the cavity 52 so as to be in mesh with the teeth 27 of the rack 26. Thus, if the handle 46 is turned, its rotation is decelerated and transmitted to the third gear 53 by the first and second gears 45 and 51. Then, the third gear 53 causes the rack 26 to slide, thereby advancing or retreating the operating wire 9 through the medium of the coupling rod 16. Thus, the first to third gears 45, 51 and 53 constitute a speed reduction mechanism 54 in the present invention.

The operation of the crushing apparatus with the above described construction will now be described.

First, the flexible sheath 1, with the operating section 18 removed from the connector 3, is inserted into a forceps channel of an endoscope (not shown), and the endoscope, along with the flexible sheath 1, is introduced into a body cavity. The sheath 1 is projected from the distal end of the endoscope and inserted into, for example, a bile duct through a duodenal papilla. Subsequently, the operating section 18 is coupled to the connector 3. Namely, the extreme end of the coupling rod 16 is fixed to the handle grip portion 32 by means of the retaining rod 37, the second member 6 of the connector 3 is inserted into the connecting ring 24, and the connector is fixed by means of the setscrew 25.

Figure 5:
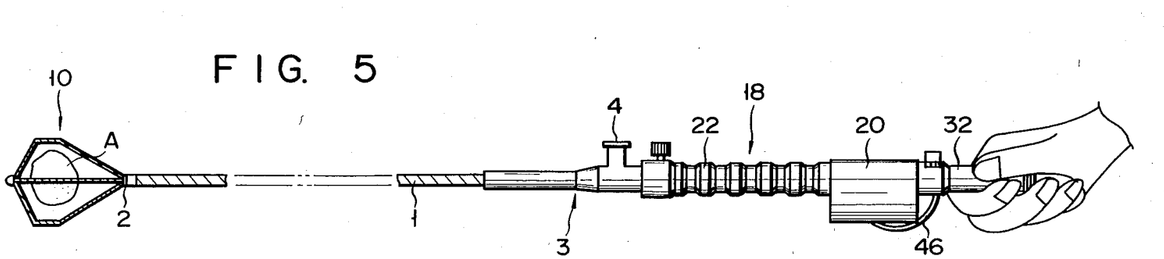
Figure 6:
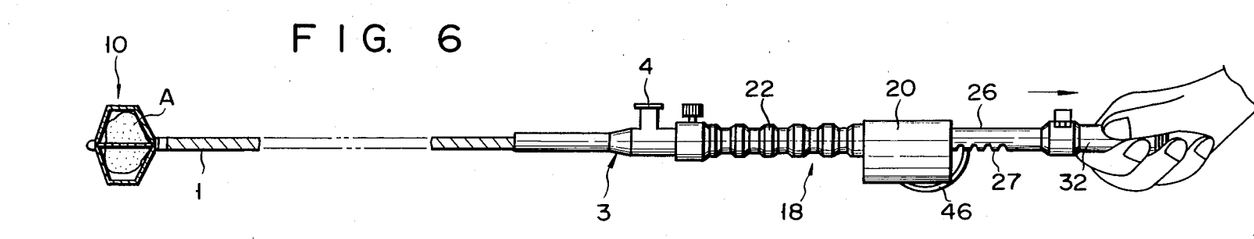

Then, if a calculus A as shown in FIG. 5 is detected as a result of an endoscopic observation of the bile duct, the handle grip portion 32 is pushed into the body 20 to advance the operating wire 9 together with the rack 26. As a result, the basket 10 projects from the distal end of the flexible sheath 1 and is opened. After the basket 10 is opened, the calculus A is taken into it through the gaps between the elastic wires 11. Then, the handle grip portion 32 is drawn out from the body 20 to contract the basket 10, as shown in FIG. 6. These advancing and retreating operations for the operating wire 9 can be quickly performed with ease by handling the handle grip portion 32. Therefore, even if the calculus A slips out of the basket 10, it can easily be taken again into the basket.

Figure 7:
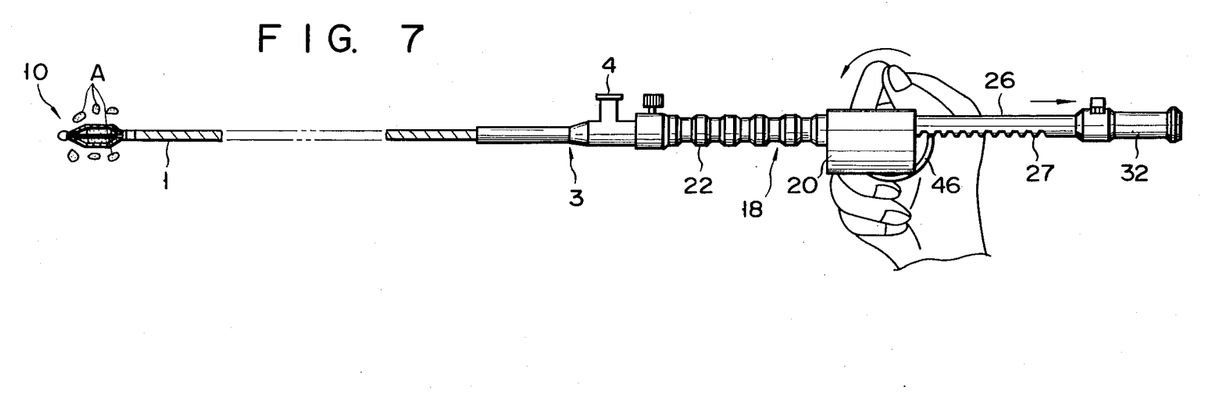

If the calculus A seized by the basket 10 is too bulky to be taken out from the bile duct, the handle 46 of the operating section 18 is rotated in a direction such that the rack 26 is retreated or projected from the body 20. Thereupon, the operating wire 9 is moved in association with the movement of the rack 26 to draw the basket 10 into the flexible sheath 1, thereby contracting the basket 10. As a result, the calculus A is squeezed and crushed by the elastic wires 11 of the basket 10. At this time, the rotation of the hand 46 is decelerated by the reduction mechanism 54 and transmitted to the rack 26. Thus, the moving speed of the rack 26, i.e., the contracting speed of the basket 10, is lower than the rotating speed of the handle 46. Accordingly, the calculus A is crushed relatively slowly, so that it will never forcibly scatter to injure the inner wall of the bile duct. An operative force applied to the handle 46 is amplified by the speed reduction mechanism 54 or the first to third gears 45, 51 and 53, and transmitted to the rack 26. Thus, the calculus A can be fully crushed by rotating the handle 46 even with a relatively small force.

Alternatively, in crushing the calculus A, the handle grip portion 32 may be slid back and forth with the calculus A held in the basket 10 so that the calculus A is repeatedly run against the rigid portion 2 at the forward end of the flexible sheath 1.

According to this embodiment, as described in detail above, the rotation of the handle at the operating section is transmitted to the rack through the speed reduction gear, and the operating wire is moved in association with the movement of the rack to contract the basket, thereby crushing the calculus. Accordingly, the operative force applied to the handle can be gradually transmitted to the operating wire after it is amplified, so that the calculus can be crushed with a relatively small operative force without forcibly scattering it. Also, the operating wire may be operated by means of the handle grip portion coupled to the rack without the use of the handle. In this case, the operating wire advances and retreats at the same speed as the moving speed of the handle grip portion, so that the basket can be opened and closed quickly and easily.

Figure 8:
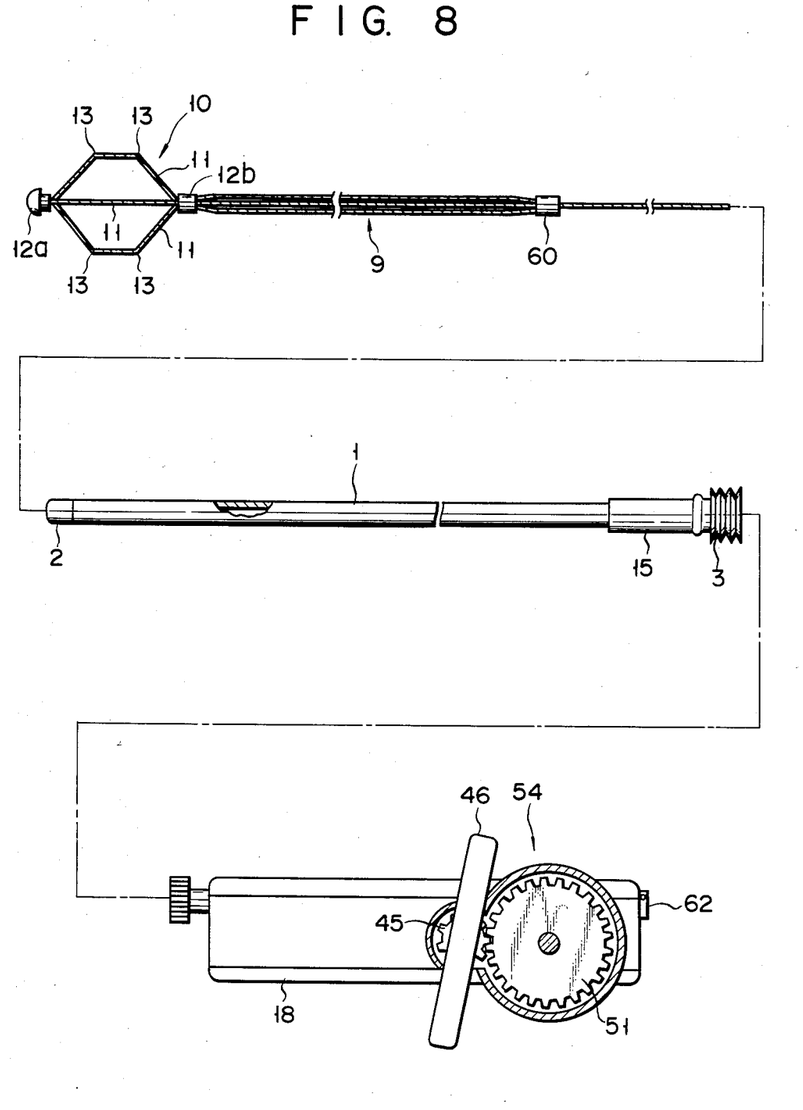
FIG. 8 is an exploded side view of the apparatus.
Figure 9:
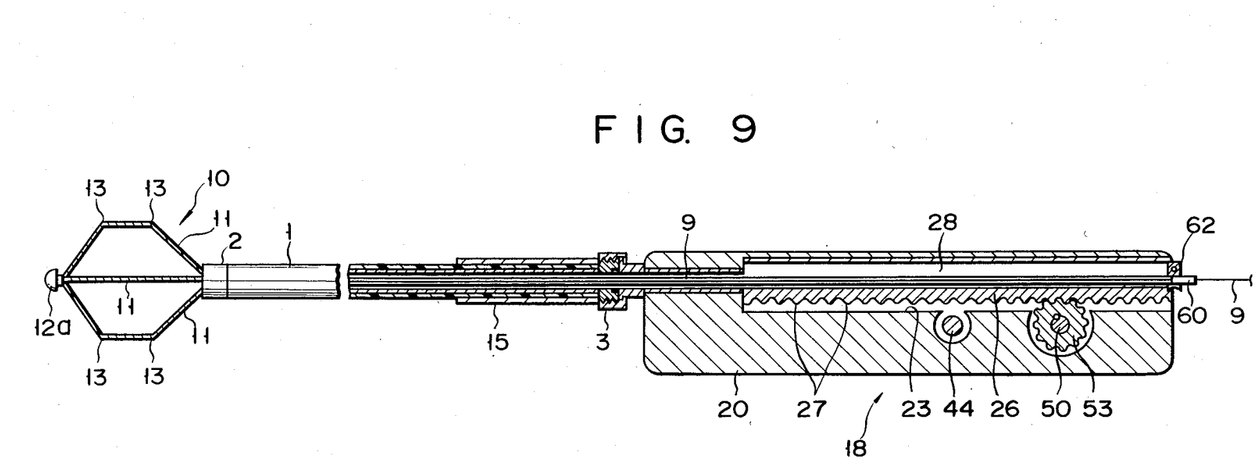
FIG. 9 is a sectional view of an operating section of the apparatus.
Figure 10:
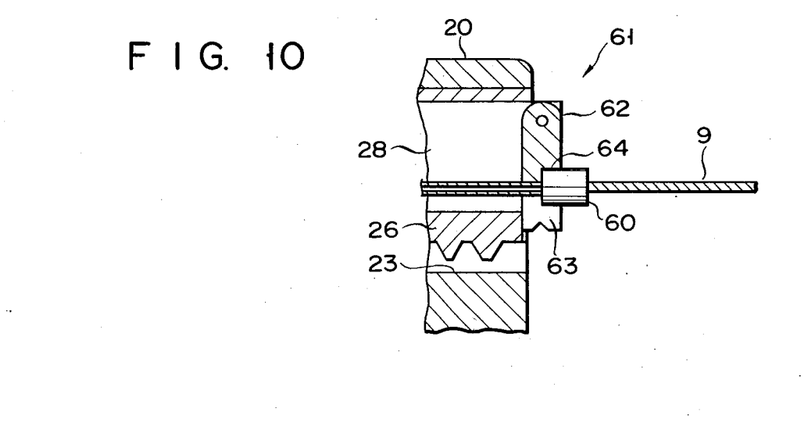
FIG. 10 is an enlarged sectional view showing part of the operating section.

FIGS. 8 to 10 show a crushing apparatus according to a second embodiment of the present invention. In FIGS. 8 to 10, like reference numerals are used to designate like members used in the first embodiment, and a description of those members is omitted. The following is a detailed description only of differences between the first and second embodiments.

In this second embodiment, a basket 10 is formed by coupling the respective distal ends and middle portions of a plurality of elastic wires 11 by means of chips 12a and 12b, respectively, and providing, e.g., two bent portions 13 in the middle of each elastic wire 11. The wires 11 extend rearward from the chip 12b, and one of them extends longer than the others. The respective rear ends of the remaining wires 11 are coupled to the longer wire 11 by means of a retainer 60. Those portions of the elastic wires 11 which extend rearward from the chip 12b constitute an operating wire 9.

A flexible sheath 1 is formed by covering a closely wound coil with a covering material, and is connected to an operating section by means of a connector 3 whose outer peripheral surface is threaded.

In this embodiment, the operating means is not provided with a handle grip portion, and the operating wire 9 is connected to a rack 26. Namely, as shown in FIGS. 9 and 10, the operating wire 9 inserted into the body 20 of the operating section 18, passes through a guide groove 28 of the rack 26, and extends rearward from the body 20. The rack 26 is fitted at its rear end with a swingable retaining flap 62 which serves to open and close the rear end of the guide groove 28. The operating wire 9 is coupled to the rack 26 by causing the retainer 60 of the operating wire 9 to engage the retaining flap 62. Thus, the retaining flap 62 and the retainer 60 constitute coupling means 61 in the present invention. The retaining flap 62 is formed with a slit 63 which permits passage of the operating wire 9 and prevents passage of the retainer 60, and a recess 64 which receives the retainer 60 and prevents unexpected movement of it. If a handle 46 is turned with the retainer 60 of the operating wire 9 kept in engagement with the retaining flap 62, the rack 26 is slid by a speed reduction mechanism 54. Thus, the operating wire 9 advances and retreats.

Also in the second embodiment constructed in this manner, as in the first embodiment, the rack 26 and the operating wire 9 are moved by an operative force decelerated and amplified by the speed reduction mechanism, so that a calculus can be crushed with a relatively small operative force without scattering. Moreover, the basket and the operating wire are formed from common elastic wires, so even if a great tensile force is applied to the basket at the time of the crushing of the calculus, the basket can be prevented from coming off the operating wire to be left in the body.

Figure 11:
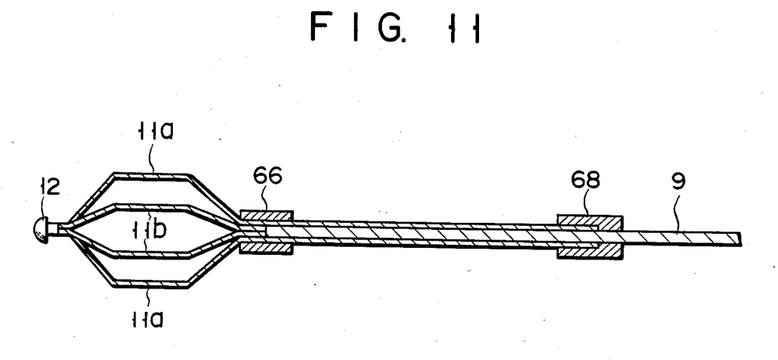
FIG. 11 is a side view showing a modified example of a basket.

The present invention is not limited to the embodiment described above, and various changes and modifications may be effected therein by one skilled in the art without departing from the scope or spirit of the invention. For example, the basket and operating wire may be constructed as shown in FIG. 11. In this modified example, the basket 10 is formed from a long elastic wire 11a and a relatively short elastic wire 11b. The wires 11a and 11b are each folded double, and their respective folds are coupled together by means of a distal end chip 12. Both ends of the shorter wire 11b, middle portions of the longer wire 11a, and the distal end portion of the operating wire 9 are coupled together by means of a first fixed ring 66. Both end portions of the longer wire 11a extend rearward along the operating wire 9, and its extreme ends are coupled to the operating wire 9 by means of a second fixed ring 68. The operating wire 9 extends rearward from the first fixed ring 66 through the second fixed ring 68.

The basket thus constructed can provide the same function and effect as the basket used in the second embodiment.

Figure 12:
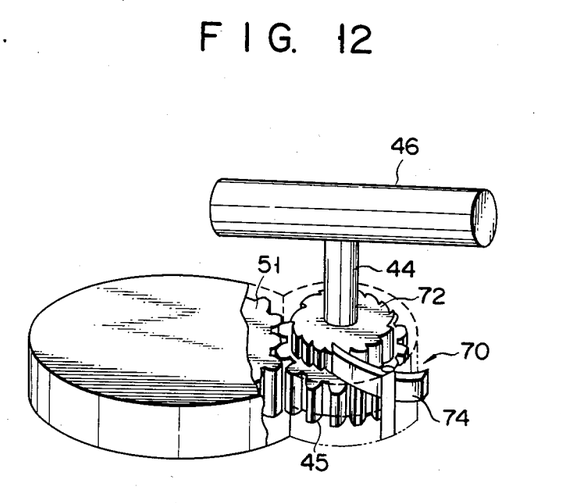
FIG. 12 is a perspective view showing a modified example of a speed reduction mechanism.

As shown in FIG. 12, moreover, the operating means may be provided with, e.g., a ratchet mechanism 70 as means for preventing the speed reduction mechanism from rotating reversely at the time of the crush. The ratchet mechanism 70 includes a reversal preventing gear 72 coaxially fixed to the first gear 45 and a stopper 74 which is in mesh with the gear 72 and allows it to rotate only in the forward direction. The ratchet mechanism 70 prevents the handle 46 from being rotated reversely by a resistance produced by the crush.

In all of the embodiments and modifications described above, the calculus is crushed by the use of human power. However, a drive source, such as a motor, may be used in place of human power.

What is claimed is:

1. A crushing apparatus for crushing a calculus produced in a body cavity, comprising:
a flexible sheath having a proximal end and a distal end and including a rigid portion at the distal end and adapted to be inserted into the body cavity;
an operating wire longer than the sheath and slidably inserted into the sheath and having a proximal end portion and a distal end portion;
a collapsible basket for seizing the calculus, said basket including a plurality of elastic wires coupled to the distal end portion of the operating wire and extending from the distal end of the sheath;

a body removably connected to the proximal end of the sheath;

a rack slidably arranged in the body and coupled to the proximal end portion of the operating wire, to be slidable together with the operating wire;

and first and second operating means for selectively sliding said rack and thereby sliding said operating wire relative to said sheath so as to expand or contract said basket;

said first operating means including a handle grip portion connected to said rack and extending outwardly from the body for sliding said rack directly by hand;

said second operating means including an operating handle mounted on said body so as to be freely rotatable with respect to and unobstructed by said body, and also including a speed reduction and force amplifying mechanism including a plurality of meshing gears of different sizes interposed between said operating handle and said rack such that a rotary speed and a rotary force applied to said operating handle are transmitted to said rack and thereby to said operating wire as a reduced speed and an amplified force, respectively.

2. A crushing apparatus according to claim 1, wherein said speed reduction and force amplyifying mechanism includes a first gear rotatably mounted on said body, a second gear having more teeth than said first gear and rotatably mounted on said body and in mesh with said first gear, and a third gear disposed in said body to be rotatable together with said second gear and in mesh with said rack, said operating handle being coupled to said first gear to rotate together therewith.

3. A crushing apparatus according to calim 1, wherein said operating means includes coupling means for removably coupling said operating wire to said rack.

4. A crushing apparatus according to claim 3, wherein said coupling means includes a retaining portion fixed to the proximal end portion of said operating wire, and a retaining member rockably attached to the rack and in engagement with said retaining portion, said retaining member having a slit penetrated by said operating wire and an engaging portion receiving said retaining portion.

5. A crushing apparatus according to claim 1, wherein respective distal ends of the plurality of elastic wires are coupled together, portions of the elastic wires distant from the distal ends are coupled together, portions of the elastic wires between the distal ends and the distant portions are bent, and portions of the elastic wires which extend from the distant portions constitute the operating wire.

6. A crushing apparatus according to claim 1, wherein the elastic wires form a double fold each, the respective folds being coupled, middle portions and both ends of the elastic wires being fixed to the distal end portion and a middle portion of the operating wire, and bent portions are formed between the fold and the middle portion of each elastic wire.

7. A crushing apparatus according to claim 1, wherein said speed reduction and force amplifying mechanism includes a ratchet for preventing the gears from rotating reversely.

* * * * *